(12) United States Patent
Ouda et al.

(10) Patent No.: US 12,312,303 B2
(45) Date of Patent: May 27, 2025

(54) METHOD FOR PRODUCING POLYOXYMETHYLENE DIMETHYL ETHERS

(71) Applicant: Fraunhofer-Gesellschaft zur Förderung der angewandten Forschung e.V., Munich (DE)

(72) Inventors: Mohamed Ouda, Freiburg (DE); Franz Mantei, Freiburg (DE); Achim Schaadt, Freiburg (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 540 days.

(21) Appl. No.: 17/612,386

(22) PCT Filed: May 18, 2020

(86) PCT No.: PCT/EP2020/063774
§ 371 (c)(1),
(2) Date: Nov. 18, 2021

(87) PCT Pub. No.: WO2020/234220
PCT Pub. Date: Nov. 26, 2020

(65) Prior Publication Data
US 2022/0388935 A1    Dec. 8, 2022

(30) Foreign Application Priority Data

May 23, 2019   (DE) .................... 10 2019 207 540.1

(51) Int. Cl.
*C07C 41/58*   (2006.01)
*C07C 41/56*   (2006.01)

(52) U.S. Cl.
CPC .............. *C07C 41/58* (2013.01); *C07C 41/56* (2013.01)

(58) Field of Classification Search
CPC .......... C07C 41/58; C07C 41/56; Y02P 20/10
See application file for complete search history.

(56) References Cited

U.S. PATENT DOCUMENTS

| | | | | |
|---|---|---|---|---|
| 4,302,356 A | * | 11/1981 | Smith, Jr. ................ | B01J 35/56 502/159 |
| 6,350,919 B1 | * | 2/2002 | Hagen ..................... | C10L 10/02 568/613 |
| 6,392,102 B1 | | 5/2002 | Hagen et al. | |
| 8,987,521 B2 | | 3/2015 | Xia et al. | |
| 10,377,689 B2 | | 8/2019 | Burger et al. | |
| 2018/0134642 A1 | * | 5/2018 | Burger ..................... | B01D 3/009 |

FOREIGN PATENT DOCUMENTS

| | | | | |
|---|---|---|---|---|
| CN | 1305444 | A | 7/2001 | |
| CN | 101346403 | A | 1/2009 | |
| CN | 102372611 | A1 | 3/2012 | |
| CN | 102372615 | A | 3/2012 | |
| CN | 104136400 | A | 11/2014 | |
| CN | 104557483 | A | 4/2015 | |
| CN | 104694150 | A | 6/2015 | |
| CN | 109651099 | A | 4/2019 | |
| CN | 110078599 | * | 8/2019 | ............ B01D 3/009 |
| DE | 102004053839 | A1 | 5/2006 | |
| DE | 102017218782 | A1 | 4/2019 | |
| EP | 3323800 | A1 | 5/2018 | |
| WO | 99/64380 | A1 | 12/1999 | |
| WO | 2006/134088 | A1 | 12/2006 | |
| WO | 2007/051658 | A1 | 5/2007 | |
| WO | WO-2019077140 | A1 * | 4/2019 | ............ B01J 23/881 |

OTHER PUBLICATIONS

Daramola et al. ("Potential Applications of Zeolite Membranes in Reaction Coupling Separation Processes", Materials, Oct. 2012, Issue 5, pp. 2101-2136). (Year: 2012).*
Ouda, M., et al. "Poly (oxymethylene) dimethyl ether synthesis a combined chemical equilibrium investigation towards an increasingly efficient and potentially sustainable synthetic route." Reaction Chemistry & Engineering 2.1 (2017): 50-59.
Ouda, Mohamed, et al. "A hybrid description and evaluation of oxymethylene dimethyl ethers synthesis based on the endothermic dehydrogenation of methanol." Reaction Chemistry & Engineering 3.5 (2018): 676-695.
Liu, Haoye, et al. "Recent progress in the application in compression ignition engines and the synthesis technologies of polyoxymethylene dimethyl ethers." Applied Energy 233 (2019): 599-611.
Chinese Application No. 202080036809.3, Office Action dated Sep. 19, 2023.
Baranowski, Christophe, Catalytic synthesis of polyoxymethylene dimethyl ethers (OME): A review, Applied Catalysis B: Environmental 217 (2017) 407-420.
Zheng, et al. Progress and Prospect of Polyoxymethylene dimethyl ethers, Chemical Industry and Engineering Progress, 2016, 35, 8.

* cited by examiner

*Primary Examiner* — John S Kenyon
*Assistant Examiner* — Xiaobin Ding
(74) *Attorney, Agent, or Firm* — Tarolli, Sundheim, Covell & Tummino LLP

(57) ABSTRACT

The present invention relates to a method for producing polyoxymethylene dimethyl ether by introducing
a formaldehyde source and
at least one compound of the formula (I)

$$H_3C-O-R \qquad (I)$$

Figure 1:
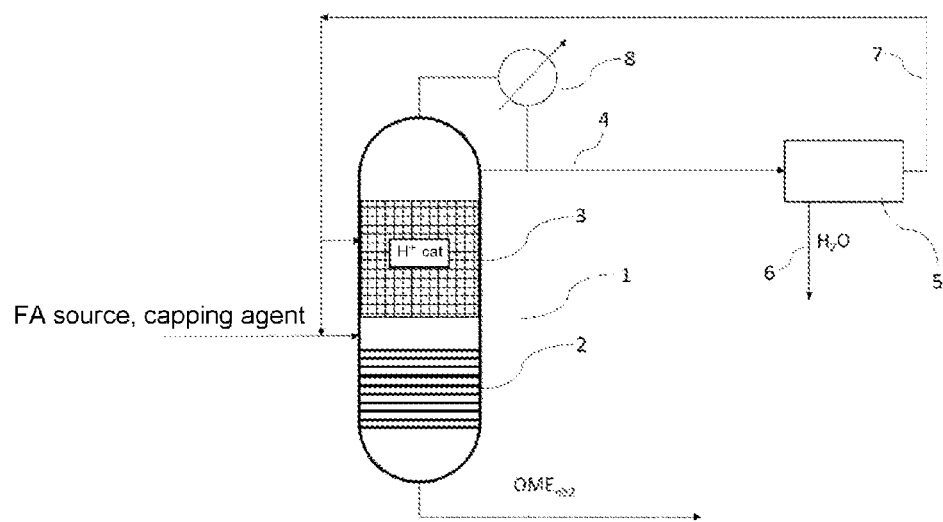

where
R is H or $-(CH_2O)_x-CH_3$ with x being 0 or 1
as reactants into a reactive distillation unit and reacting them to give polyoxymethylene dimethyl ether, wherein the method produces polyoxymethylene dimethyl ether exclusively in the reactive distillation unit.

12 Claims, 3 Drawing Sheets

METHOD FOR PRODUCING POLYOXYMETHYLENE DIMETHYL ETHERS

The present invention relates to a method for producing polyoxymethylene dimethyl ether in a reactive distillation unit.

Synthetic energy sources which are not produced on the basis of crude oil or natural gas have the ability to reduce the dependency on fossil energy sources and also the environmental pollution arising from the use of such fossil energy sources. One example of such a synthetic energy source are polyoxymethylene dimethyl ethers (OMEs). Polyoxymethylene dimethyl ethers (OMEs) can be produced from carbon dioxide and water and when employed as automotive fuel, provided that regenerative energy sources are used for producing them, exhibit a closed carbon dioxide circuit.

Furthermore, the utilization of the polyoxymethylene dimethyl ethers as energy sources offers further advantages. Polyoxymethylene dimethyl ethers do not have any carbon-carbon bonds and additionally possess a high proportion of oxygen. Polyoxymethylene dimethyl ethers burn without soot and so are gentle both to the internal combustion engine and downstream filter elements and to the environment. In this context, polyoxymethylene dimethyl ether having three to five oxymethylene units ($OME_{3-5}$) is of particular interest.

At present there are two production methods in particular used for $OME_{3-5}$, which are based on polyaddition or polycondensation reactions.

Polyaddition:

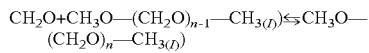

Polycondensation with Hemiacetal Formation:

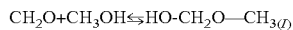 HF

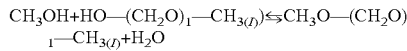 OME1

 MG

HF: poly(oxymethylene) hemiformal
MG: poly(oxymethylene) glycol

Reactants typically used in the synthesis of polyoxymethylene dimethyl ether are a formaldehyde source (e.g. formaldehyde, trioxane or paraformaldehyde) and a compound for methyl capping such as methanol, methylal or dimethyl ether (i.e., a compound which is able to convert a hydroxyl group into a methoxy group).

An overview of known production methods for polyoxymethylene dimethyl ethers is found in the following publications:

M. Ouda et al., React. Chem. Eng., 2017, 2, pp. 50-59;
M. Ouda et al., React. Chem. Eng., 3, 2018, pp. 676-695
Z. Wang et al., Applied Energy, 233-234 (2019), pp. 599-611.

The reactions of the reactants to give the polyoxymethylene dimethyl ethers typically require the presence of a catalyst, more particularly the presence of an acidic catalyst. Examples of known solids which can act as catalysts in the polyoxymethylene dimethyl ether synthesis are ionic exchange resins containing acidic groups (i.e., cation exchange resins), zeolites, aluminosilicates, transition metal oxides (which may optionally be present on a carrier material), and graphene oxide. Examples of liquid catalysts which can be used for the polyoxymethylene dimethyl ether synthesis are mineral acids (e.g., sulfuric acid), organic acids (e.g., HCOOH), and acidic ionic liquids.

Condensation reactions of the reactants in the polyoxymethylene dimethyl ether synthesis result in water being formed. It is also possible for the reactants fed to the reactor to contain water already, with consequent introduction of water into the reaction system.

In order to maximize the yield of polyoxymethylene dimethyl ether, the water must be separated off. However, if formaldehyde is present in a relatively high concentration, the efficient removal of water proves very difficult.

Water removal may be accomplished, for example, by membranes (e.g., by pervaporation or vapor permeation). Examples of membranes that can be used are polymer membranes such as PVA membranes. Investigations by the applicant have shown, however, that at relatively high formaldehyde concentrations, the long-term stability of PVA membranes is not sufficient.

As already mentioned above, one of the reactants for the synthesis of polyoxymethylene dimethyl ether is a formaldehyde source. In light of the environmentally hazardous properties of formaldehyde, the reaction plant for the polyoxymethylene dimethyl ether synthesis must be designed such that there is no release of formaldehyde. In this connection it would be advantageous if formaldehyde were to be converted as quantitatively as possible in the OME synthesis and if there was no need for downstream removal of unreacted formaldehyde.

EP 3 323 800 A1 describes a method for producing polyoxymethylene dimethyl ether by feeding formaldehyde, methanol and water into a reactor R and reacting them to give a mixture which comprises, in addition to the polyoxymethylene dimethyl ether, formaldehyde, water, methylene glycol, polyoxymethylene glycols, methanol, hemiformals and methylal. This polyoxymethylene dimethyl ether-containing mixture is introduced into a distillation unit and separated into a low-boiler fraction and high-boiler fraction.

CN 104557483 A describes the production of polyformaldehyde dimethyl ether from methanol, methylal and polyformaldehyde.

It is an object of the present invention to produce polyoxymethylene dimethyl ether (more particularly those containing three to five oxymethylene units) by way of a method which is easy to be implemented and exhibits high efficiency.

The object is achieved by means of a method for producing polyoxymethylene dimethyl ether by introducing
(i) a formaldehyde source and
(ii) at least one compound of the formula (I)

where
R is H or $-(CH_2O)_x-CH_3$ with x being 0 or 1
as reactants into a reactive distillation unit and reacting them to give polyoxymethylene dimethyl ether, wherein the method produces polyoxymethylene dimethyl ether exclusively in the reactive distillation unit.

Within the present invention it has been recognized that the formaldehyde source and the compound for methyl capping (i.e., compound (I)) can be reacted very efficiently in a reactive distillation unit to give polyoxymethylene dimethyl ether, with the possibility of substantially complete reaction of the formaldehyde being achieved. Since the top product obtained in the reactive distillation unit (also referred to as low-boiler fraction) contains relatively little formaldehyde or is even formaldehyde-free, efficient removal of water is possible. In comparison to a method which produces the polyoxymethylene dimethyl ethers from the reactants in a first step and then separates the reaction mixture into the fractions in a second step, the one-stage process of the present invention is thermodynamically advantaged. Since, moreover, the polyoxymethylene dimethyl ethers are synthesized exclusively in the reactive distillation unit, there is no need for an upstream reactor for the OME synthesis. This enables the realization of a substantially more compact plant.

The formaldehyde source is, for example, formaldehyde (e.g., as aqueous formaldehyde solution (formalin)), trioxane or paraformaldehyde.

For the method of the present invention it is possible for example to use commercially available formaldehyde (e.g., as aqueous formaldehyde solution (formalin)) and commercially available methylal. It is alternatively possible within the present invention also to generate the formaldehyde and the methylal via oxidative dehydrogenation of methanol. The production of a mixture comprising formaldehyde and methylal by oxidative dehydrogenation of methanol is described in DE 10 2017 218 782 A1.

The molar ratio of the compound of the formula (I) introduced into the reactive distillation unit to the formaldehyde (i.e., n(compound (I))/n(formaldehyde)) may be varied over a relatively wide range within the present invention and is situated for example in the range from 100/1 to 1/10. If the formaldehyde source is trioxane or paraformaldehyde, the molar amount of the formaldehyde refers to the amount of formaldehyde bound chemically in trioxane or paraformaldehyde (i.e., to the molar amount of —$CH_2$—O units in these compounds).

The method of the invention enables high flexibility in terms of reactant composition (high feedstock flexibility). For example, the reactants introduced into the reactive distillation unit may be rich in methylal or rich in methanol.

The reactive distillation unit (e.g., a reactive distillation column) comprises, for example, one or more reaction zones each containing a catalyst (more particularly a solid catalyst), and one or more distillative separation zones. The distillative separation zone contains, for example, internals for the distillative separation, more particularly trays, dumped packings or structured packings, of the kind which are common knowledge to the skilled person. The catalyst may be immobilized in the reaction zones in a manner known to the skilled person—for example, as random packings, in the form of catalyst-filled wire mesh balls, or as shaped catalyst bodies mounted on a tray in the reaction zone.

Where the reactive distillation unit comprises two or more reaction zones, it may be preferable for there to be a distillative separation zone between two reaction zones. Catalysts for the polyoxymethylene dimethyl ether synthesis are known to the skilled person. The catalyst is typically an acidic catalyst. In this case it is possible to use solid catalysts or liquid acids. Exemplary catalysts include ion exchange resins containing acidic groups (i.e., cation exchange resins), zeolites, aluminosilicates, transition metal oxides (which may optionally be present on a carrier material), graphene oxide, mineral acids (e.g., sulfuric acid), organic acids (e.g., HCOOH), acidic ionic liquids, oxonium salts (e.g., a trimethyl oxonium salt).

The reactants may be introduced into the reactive distillation unit between a distillative separation zone and a reaction zone, for example. Within the present invention, the reactants may alternatively be introduced into the reactive distillation unit in the region of the reaction zone or of the distillative separation zone. Pressure and temperature in the reactive distillation unit are preferably selected such that the reactants introduced are converted partly or completely into the gas phase. In the reaction zone, the reactants are converted to polyoxymethylene dimethyl ether in the presence of the catalyst. In the distillative separation zone, the formaldehyde, the compound (I) (e.g. methylal and/or methanol) and the water are removed from polyoxymethylene dimethyl ether. A high-boiler fraction is obtained, comprising polyoxymethylene dimethyl ether having at least three oxymethylene units (e.g., three to five oxymethylene units). The high-boiler fraction typically further comprises $OME_2$ and/or optionally $OME_{n>5}$. Also obtained is a low-boiler fraction, comprising water and unconverted reactants. Because the method of the invention enables a very high degree of conversion of the formaldehyde source, the low-boiler fraction preferably contains only relatively small amounts of formaldehyde (e.g., less than 30 vol % or less than 20 vol %) or is even formaldehyde-free. The low-boiler fraction typically contains no $OME_{n\geq 4}$ and preferably also no $OME_3$.

In one preferred embodiment the reaction zone contains a hollow body which at least partly encloses the catalyst. Gaseous reactants which are ascending in the reactive distillation unit are able to flow through the hollow body (e.g., through openings in its bottom side and top side), but the hollow body substantially prevents contact between the catalyst and liquid polyoxymethylene dimethyl ether which is running back downward in the reactive distillation unit. For example, the liquid polyoxymethylene dimethyl ether runs at least partly or even exclusively laterally past the hollow body. The hollow body may be tubular or bell-shaped, for example. Other geometries, however, are likewise possible. The hollow body may be made, for example, of a metal or a ceramic. A gas flowing upward in the reactive distillation unit penetrates the container, for example, via an opening in its bottom side and is able to depart the container via an opening in its top side. If a liquid polyoxymethylene dimethyl ether is running back downward in the reactive distillation unit, it is unable to run into the hollow body, or is able to run into the hollow body only to a small extent, owing to the gas flowing out at the top side of the hollow body, and instead it flows laterally past the hollow body. This measure reduces the reverse reaction of long-chain polyoxymethylene dimethyl ether that has already been formed back into short-chain compounds.

The reaction zone may be surrounded at least partly by a membrane. The membrane enables the selective removal of particular components from the reaction zone. The membrane is preferably a water-permeable membrane, allowing water to be removed from the other components in the reaction zone via this membrane. This measure enables an even higher degree of conversion of the reactants. The membrane may be tubular, for example. Other geometries, however, are likewise possible. If the reactive distillation unit comprises two or more reaction zones, the membrane may take the form, for example, of a tube which surrounds at least two of the reaction zones. In this illustrative embodiment, then, the reactive distillation unit accommodates a tubular membrane which encloses two or more reaction zones (optionally all of the reaction zones present). Suitable membranes, especially those for the removal of water, are known to the skilled person. The membrane may be an inorganic membrane or a polymer membrane. The inorganic membrane is, for example, a ceramic membrane or a zeolite membrane.

The distillative separation zone may optionally contain a basic material (e.g., a basic ion exchange resin). Where an acidic catalyst material is carried from the reaction zone into the distillative separation zone, it may be neutralized by the basic material present in the distillative separation zone.

The distillative separation zone is preferably catalyst-free, thus containing no catalyst for the polyoxymethylene dimethyl ether synthesis.

In the method of the invention, the reactive distillation unit may be operated under relatively mild conditions: for example, at a pressure in the range from 0.1 to 10 bar, more preferably 0.2 bar to 5 bar, even more preferably 0.2 bar to 1 bar; and at a temperature in the range of 20-300° C., more preferably 50° C. to 200° C., even more preferably 50° C. to 150° C.

The reactive distillation unit is operated in the reaction zone, for example, with a weight hourly space velocity (WHSV) of 0.1-150 h$^{-1}$, more preferably 1-150 h$^{-1}$, even more preferably 5-50 h$^{-1}$. WHSV indicates the ratio between the mass flow rate of reactant and the weight of catalyst employed.

The reactive distillation unit may comprise an evaporator ("reboiler") and a condenser. This is known to the skilled person.

The high-boiler fraction collects at the bottom of the reactive distillation unit and is therefore also referred to as the bottom product or column bottoms. After being taken off from the reactive distillation unit, the high-boiler fraction may optionally be subjected to further distillations (e.g., a fractional distillation) in order to isolate the desired polyoxymethylene dimethyl ether fractions (more particularly the OME$_{3-5}$ fractions).

In one preferred embodiment the low-boiler fraction is introduced into a separating unit to give a low-water or water-free stream and a water-rich stream.

The separating unit may be located, for example, outside the reactive distillation unit. Alternatively it is also possible for the separating unit to be located in the reactive distillation unit, in its top region, for example. The low-boiler fraction may optionally be subjected to partial or complete liquefaction by a condenser unit before being introduced into the separating unit. As already mentioned above, the separating unit generates a low-water or water-free stream and a water-rich stream.

The removal of the water in the separating unit is accomplished for example by a liquid-liquid phase separation (a liquid-liquid phase demixing for example), a pervaporation or vapor permeation (using one or more membranes, for example), an adsorption, an absorption, a thermal phase separation or an extraction.

In the case of liquid-liquid phase separation, a miscibility gap and density differences between the water and the organic components, for example, are utilized.

Suitable membranes for the pervaporation or vapor permeation are known to the skilled person. Polymer membranes or inorganic membranes may be used. Suitable materials for the removal of water by adsorption are likewise known to the skilled person, such as zeolites, activated carbon, metal oxides, silica gels, or salts.

Within the present invention, the separating unit may be connected thermally to the evaporator ("reboiler") and/or the condenser of the reactive distillation unit. As a result of this measure, the energy requirements of the separating unit can be covered at least partly by the evaporator and/or the condenser.

The low-water or water-free stream is preferably returned at least partly to the reactive distillation unit. This recycling may be accomplished, for example, by feeding the low-water or water-free stream to the reactants outside the reactive distillation unit and feeding it with them into the reactive distillation unit. Additionally or alternatively, the low-water or water-free stream may be returned directly into the reactive distillation unit, in the region of the reaction zone of the reactive distillation unit, for example. By varying the recycle ratio (i.e., the fraction of the low-water or water-free stream that is returned to the reactive distillation unit) it is also possible to control the composition of the end product.

The method of the invention features a very high efficiency, of more than 60%, for example. The method efficiency may be determined with the following formula:

$$\eta_{eff} = \frac{(\dot{m}_i\, LHV_i)_{product}}{(\dot{m}_i\, LHV_i)_{feed} + E_{process}}$$

where $\eta_{eff}$ is the method efficiency, $\dot{m}_i$ is the mass flow rate of component i, $LHV_i$ is the lower heating value of component i, and $E_{process}$ is the energy requirement for the method.

The present invention is now elucidated in more detail with reference to an illustrative embodiment which is represented schematically in FIG. 1.

The reactive distillation unit 1 comprises a distillative separation zone 2 and a reaction zone 3. The distillative separation zone comprises internals known to the skilled person for distillative separation, examples being trays, dumped packings or structured packings. The reaction zone 3 contains an acidic catalyst which catalyzes the conversion of the reactants to give polyoxymethylene dimethyl ether.

A formaldehyde source ("FA source", e.g., formaldehyde, trioxane or paraformaldehyde) and also a capping agent (i.e., a compound which is able to convert a hydroxyl group into a methoxy group) such as MeOH, methylal or dimethyl ether, for example, are introduced as reactants into the reactive distillation unit 1. The feed into the reactive distillation unit 1 may optionally also include water.

The reactant stream is introduced into the reactive distillation unit 1, for example, at a temperature and a pressure which result in the reactants being converted partly or completely into the gas phase. The reactants ascend in the catalyst-containing reaction zone 3, where they react to give polyoxymethylene dimethyl ether. As a result of condensation reactions, water may also be formed in the reaction zone 3.

The polyoxymethylene dimethyl ether formed in the reaction zone 3 runs downward and enters the distillative separation zone 2, where the polyoxymethylene dimethyl ether is separated from unconverted reactants and water.

The high-boiler fraction collects at the bottom of the reactive distillation unit 1 and consists substantially of polyoxymethylene dimethyl ether. The high-boiler fraction is taken off from the reactive distillation unit 1 and may be optionally subjected to further work-up steps (e.g., a fractional distillation).

In the reaction zone 3, the formaldehyde is consumed very largely or even completely with continuous formation of polyoxymethylene dimethyl ether. The low-boiler fraction, which is taken off as top product from the reactive distillation unit 1 via line 4, comprises water, but is substantially formaldehyde-free. Besides water, the low-boiler fraction comprises, for example, one or more compounds of the formula (I) (e.g., methylal and/or methanol). Optionally there may be OME$_2$ in the low-boiler fraction.

After optional liquefaction by a condenser 8, the low-boiler fraction is fed to a separating unit 5. In this separating unit 5, a water-rich stream 6 and also a low-water or water-free stream 7 are generated. The low-water or water-free stream 7 is fed to the reactant stream and introduced with it into the reactive distillation unit 1. The low-water or water-free stream 7 may also be returned directly into the reaction zone 3 of the reactive distillation unit 1.

Figure 2:
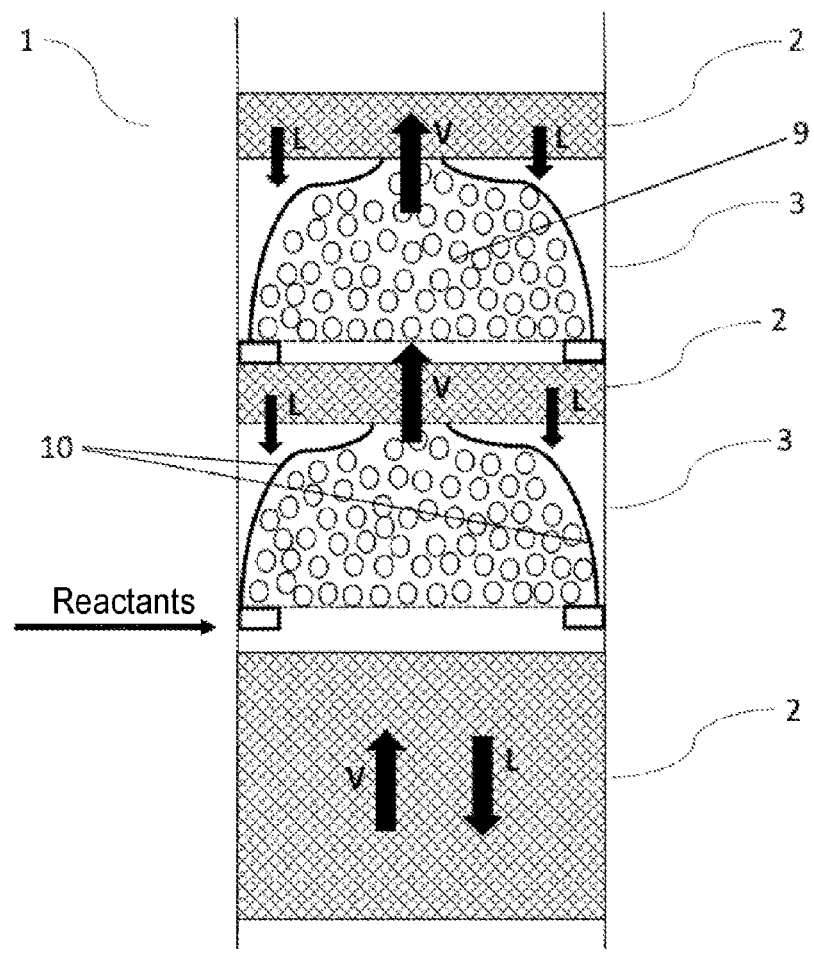

Another preferred embodiment of the invention is illustrated in FIG. 2.

FIG. 2 shows a detail of the reactive distillation unit 1 with distillative separation zones 2 and reaction zones 3. Located in each of the reaction zones 3 is a catalyst 9 (e.g., an acidic ion exchange resin). The walls of a hollow body 10 enclose the catalyst 9. The hollow body 10 is open at its top and bottom sides. Upwardly flowing gaseous compounds V can flow through the hollow body 10, whereas liquid polyoxymethylene dimethyl ether L, which is running back downward in the reactive distillation unit 1, flows at least partly laterally past the hollow body 10 and therefore makes no contact or only minimal contact, with the catalyst 9. Consequently the reverse reaction of long-chain polyoxymethylene dimethyl ether which has already been formed to short-chain compounds is reduced.

Figure 3:
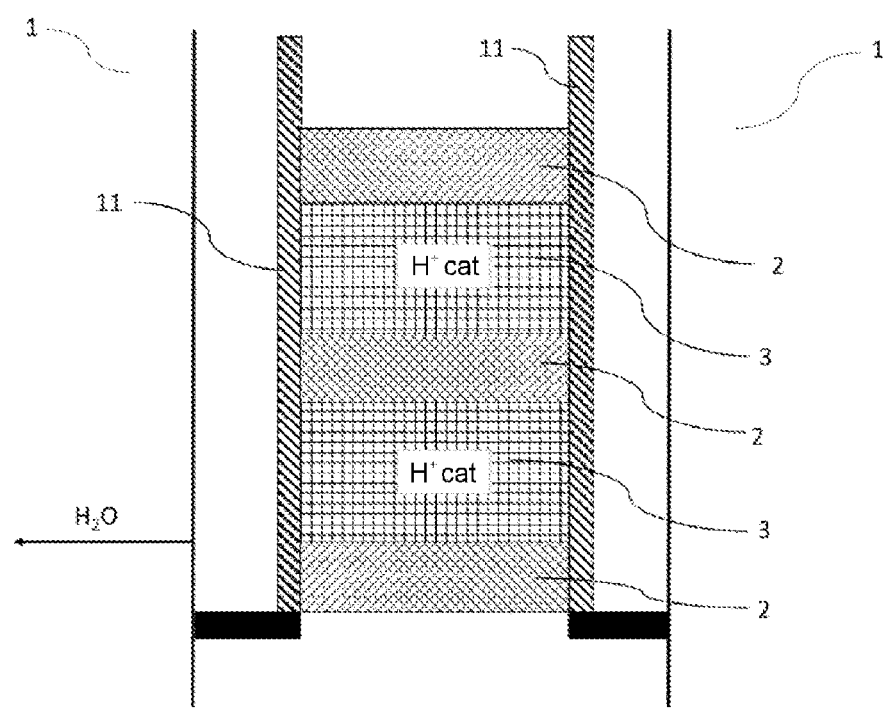

A further illustrative embodiment of the invention is illustrated in FIG. 3.

FIG. 3 shows a detail of the reactive distillation unit 1 with reaction zones 3 (each of which contains an acidic catalyst ("H+ cat")) and distillative separation zones 2. The reaction zones 3 are surrounded by a membrane 11, such as a zeolite membrane, for example. Via the water-permeable membrane 11, water can be removed from the other components in the reaction zones 3 and taken off from the reactive distillation unit as a water-rich stream. The membrane 11 may be embodied, for example, in the form of a tube which encloses one or more of the reaction zones 3.

The invention claimed is:

1. A method for producing polyoxymethylene dimethyl ether, the method comprising:
   introducing:
   i) a formaldehyde source, and
   ii) at least one compound of the formula (I)

H₃C—O—R        (I)

where;
   R is H or —(CH₂O)$_x$—CH₃ with x being 0 or 1
   as reactants into a reactive distillation unit; and
   reacting the formaldehyde source and the at least one compound of formula (I) to give polyoxymethylene dimethyl ether, wherein the method produces polyoxymethylene dimethyl ether exclusively in the reactive distillation unit;
   wherein the reactive distillation unit comprises one or more reaction zones, each containing a catalyst, and one or more distillative separation zones;
   wherein the one or more reaction zones contain a hollow body which at least partially encloses the catalyst;
   wherein gaseous reactants, which are ascending in the reactive distillation unit, are able to flow through the hollow body, but the hollow body prevents contact between the catalyst and the liquid polyoxymethylene dimethyl ether, which is running back downward to the reactive distillation unit; and
   wherein the liquid polyoxymethylene dimethyl ether which is running back downward in the reactive distillation unit runs at least partly laterally past the hollow body.

2. The method according to claim 1, wherein the catalyst in the reactive distillation unit is an acidic catalyst.

3. The method according to claim 1, wherein the reactants introduced into the reactive distillation unit are rich in methylal or rich in methanol.

4. The method according to claim 1, wherein the reactive distillation unit is operated at a pressure in the range from 0.1 to 10 bar and a temperature in the range of 20-300° C.

5. The method according to claim 1, wherein the weight hourly space velocity WHSV in the one or more reaction zones is 0.1-150 h$^{-1}$.

6. The method according to claim 1, wherein the one or more distillative separation zones contains a basic material.

7. The method according to claim 1, wherein a low-boiler fraction comprising water and unconverted reactants is introduced into a separating unit to give a low-water or water-free stream and a water-rich stream.

8. The method according to claim 7, wherein the removal of the water in the separating unit takes place by a liquid-liquid phase separation, a pervaporation, a vapor permeation, an adsorption, an absorption, a thermal phase separation or an extraction.

9. The method according to claim 7, wherein a evaporator and/or the condenser of the reactive distillation unit are/is connected thermally to the separating unit and are/is able to supply a part of the energy for the operation of the separating unit.

10. The method according to claim 7, wherein the low-water or water-free stream is returned to the reactive distillation unit.

11. The method according to claim 10, wherein the low-water or water-free stream is fed to the reactants outside the reactive distillation unit and then introduced with the reactants into the reactive distillation unit; and/or wherein the low-water or water-free stream is returned directly into the reactive distillation unit.

12. The method according to claim 1, wherein the hollow body is made of a metal or a ceramic.

* * * * *